United States Patent [19]
Sjøholm et al.

[11] Patent Number: 6,165,770
[45] Date of Patent: Dec. 26, 2000

[54] ALKALINE STABLE AMYLASE FROM THERMOALCALIBACTER

[75] Inventors: Carsten Sjøholm, Allerød, Denmark; Garabed Antranikian; Steffan Prowe, both of Hamburg, Germany

[73] Assignee: Novo Nordisk A/S, Bagsvaerd, Denmark

[21] Appl. No.: 09/271,783

[22] Filed: Mar. 18, 1999

Related U.S. Application Data

[63] Continuation of application No. PCT/DK97/00410, Sep. 26, 1997.

[30] Foreign Application Priority Data

Sep. 26, 1996 [DK] Denmark .................................. 1050/96

[51] Int. Cl.$^7$ ............................... C12N 9/28; C11D 7/42; C12S 9/00
[52] U.S. Cl. ........................... 435/202; 510/392; 510/531
[58] Field of Search ............................ 435/202; 510/392, 510/531

[56] References Cited

U.S. PATENT DOCUMENTS

| 4,600,693 | 7/1986 | Kindle et al. | 435/176 |
| 5,635,468 | 6/1997 | Ara et al. | 510/392 |
| 5,824,531 | 10/1998 | Outtrup et al. | 435/202 |

FOREIGN PATENT DOCUMENTS

| 62-019081 | 1/1987 | Japan . |
| 2049584 | 2/1990 | Japan . |

OTHER PUBLICATIONS

Ramesh et al., "Characteristics and Novel Features of Thermostable alpha–Amylase Produced by *Bacillus licheniformis* M27 under Solid State Fermentation", Starch, 42(6), pp. 233–238, Jun. 1990.

Shinke et al. (1996) Ann. NY Acad. Sci. 799:332–40.

*Primary Examiner*—Jon P. Weber
*Attorney, Agent, or Firm*—Elias J. Lambiris, Esq.; Reza Green, Esq.

[57] ABSTRACT

The present invention relates to a novel alkali stable amylase obtained from *Thermoalcalibacter bogoriae*, an enzyme composition comprising said amylase, and the use of said enzyme and enzyme composition for a number of industrial applications.

8 Claims, 4 Drawing Sheets

| Metal ion/agent | Relative amylase activity (%) | | |
| --- | --- | --- | --- |
| | 1 mM | 2 mM | 5 mM |
| MnCl$_2$ | 153 | 172 | 166 |
| CoCl$_2$ | 99 | 88 | 86 |
| EDTA | 87 | 63 | 65 |
| CaCl$_2$ | 71 | 70 | 67 |
| MgSO$_4$ | 70 | 62 | 60 |
| NaMoO$_4$ | 68 | 58 | 54 |
| ZnSO$_4$ | 65 | 73 | 68 |
| NiCl$_2$ | 62 | 60 | 70 |
| CuSO$_4$ | 46 | 42 | 38 |
| FeCl$_3$ | 51 | 36 | 0 |
| VOSO$_4$ | 49 | 50 | 0 |
| FeSO$_4$ | 42 | 4 | 0 |
| K$_2$Cr$_2$O$_7$ | 0 | 0 | 0 |
| Pefabloc SC | 215 | n.d. | 105 |
| Guanidine-HCl | 285 | n.d. | 268 |
| SDS[1] | 215 | n.d. | 5 |
| N-Bromo-succinimide | 285 | n.d. | 43 |
| DTT[2] | 358 | n.d. | 0 |

[1] sodium dodecyl sulfate, [2] dithiothreitol, *n.d.* not determined

Fig. 4

ALKALINE STABLE AMYLASE FROM THERMOALCALIBACTER

CROSS REFERENCE TO RELATED APPLICATIONS

This application is a continuation of PCT/DK97/00410 filed Sep. 26, 1997 which claims priority under 35 U.S.C. 119 of Danish application 1050/96 filed Sep. 26, 1996, the contents of which are fully incorporated herein by reference.

FIELD OF INVENTION

The present invention relates to a novel alkali stable amylase, an enzyme composition comprising said amylase, and the use of said enzyme and enzyme composition for a number of industrial applications.

BACKGROUND OF THE INVENTION

α-Amylase enzymes have been used industrially for a number of years and for a variety of different purposes, the most important of which are starch liquefaction, textile desizing, starch modification in the paper and pulp industry, and for brewing and baking. A further use of α-amylases which is becoming increasingly important is the removal of starchy stains during washing or dishwashing.

As $Ca^{2+}$ ions may disturb in industrial applications, $Ca^{2+}$ ions are undesired in e.g. laundry and dishwashing detergents, it is the object of the present invention to provide an alkali table amylase which is stable within a broad range of the metal on (e.g. $Ca^{2+}$) concentrations.

SUMMARY OF THE INVENTION

The present inventors have now surprisingly identified α-amylase from a moderately thermo alkaliphile anaerobe strain *Thermoalcalibacter bogoriae,* which belong to the Clostridium/Bacillus subphyllum.

The α-amylase of the invention has been thoroughly characterized and shown that the activity of the enzyme is relatively independent of the specific metal ion (e.g. $Ca^{2+}$) concentration, i.e. it is not activated by e.g. $Ca^{2+}$ Accordingly, in a first aspect the invention relates to an isolated α-amylase characterized by having at least 65% of residual α-amylase activity, after 30 min incubation at 65° C., pH 8.0 in a substrate solution containing (wt/vol) soluble starch (0.5%), where the substrate solution is having a $Ca^{2+}$ concentration between 0.5 mM and 6 mM $Ca^{2+}$.

The relatively high independence of the specific metal ion (e.g. $Ca^{2+}$) concentration of the α-amylase of the present invention is highly advantageous for a number of industrial applications as e.g. $Ca^{2+}$ ions may disturb in a number of industrial applications such as in laundry or dishwash detergents.

Further the α-amylase of the invention is presently believed to be the first description and characterization of extracellular amylolytic enzymes from an anaerobe thermo alkaliphile.

Accordingly, in a further aspect the present invention relates to an isolated extracellular α-amylase obtained from a strain of Thermoalcalibacter sp.

In a still further aspect the invention relates to a method of producing an α-amylase of the invention, the method comprising culturing a strain of Thermoalcalibacter sp. under conditions permitting the production of the enzyme, and recovering the enzyme from the culture.

Finally, the invention relates to an enzyme or an enzyme composition and the use of such an enzyme or enzyme composition for various industrial applications.

BRIEF DESCRIPTION OF THE DRAWINGS

The present invention is further illustrated by reference to the accompanying drawings, in which:

FIG. 1 shows electrophoretic separation of the proteins of *Thermoalcalibacter bogoriae* grown on starch. Concentrated supernatant after PD-10 (lane 1+2), α-amylase (lane 3,4,5), purified α-amylase (lane 5), CGTase (lane 6+7), silver staining (lane 1,3,5,6), activity staining (lane 2,4,7).

FIG. 4 shows the influence of metal ions and chemical reagents on amylase activity.

DEFINITIONS

Figure 1:
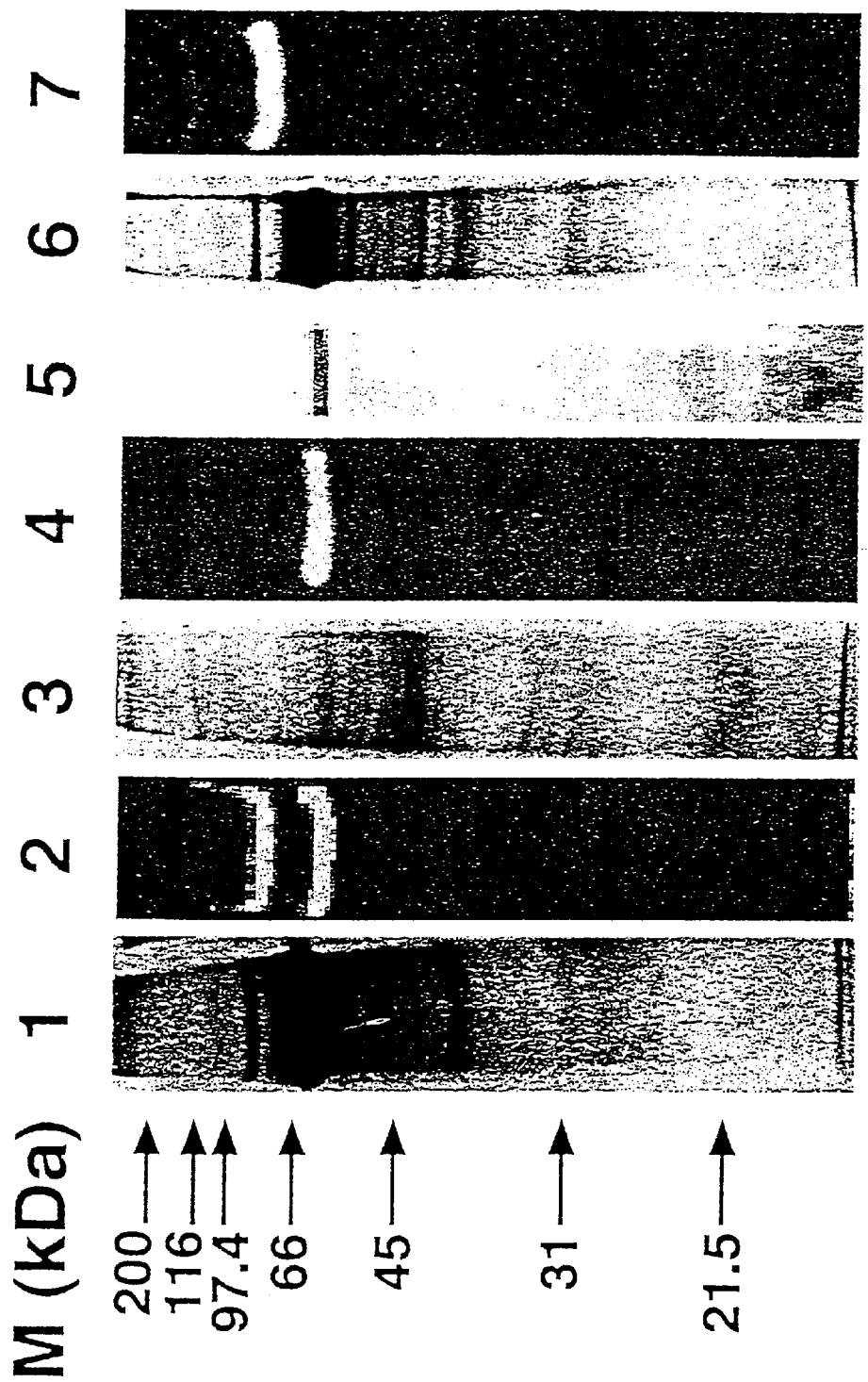
FIG. 1: SDS-PAGE of various purification steps.

Prior to discussing this invention in further detail, the following terms will first be defined.

"A cloned DNA sequence": The term "A cloned DNA sequence", refers to a DNA sequence cloned by a standard cloning procedure conventionally used in genetic engineering to relocate a segment of DNA from its natural location to a different site where it will be reproduced. The cloning process involves excision and isolation of the desired DNA segment, insertion of the piece of DNA into the vector molecule and incorporation of the recombinant vector into a cell where multiple copies or clones of the DNA segment will be replicated. The term "cloned DNA sequence" of the invention may alternatively be termed "DNA construct" or "isolated DNA sequence".

"Obtained from": For the purpose of the present invention the term "obtained from" as used herein in connection with a specific microbial source, means that the enzyme is produced by the specific source, or by a cell in which a gene from the source have been inserted.

"An isolated polypeptide": As defined herein the term, "an isolated polypeptide" or "isolated α-amylase as used about the α-amylase of the invention is a α-amylase or a α-amylase part which is essentially free of other non α-amylase polypeptides, e.g., at least about 20% pure, preferably at least about 40% pure, more preferably about 60% pure, even more preferably about 80% pure, most preferably about 90% pure, and even most preferably about 95% pure, as determined by SDS-PAGE. The term "isolated polypeptide" may alternatively be termed "purified polypeptide".

"Homologous impurities": As used herein the term "homologous impurities" means any impurity (e.g. another polypeptide than the enzyme of the invention) which originate from the homologous cell where the enzyme of the invention is originally obtained from. In the present invention the homologous cell may e.g. be a strain of *Thermoalcalibacter bogoriae.*

"α-amylase" In the present context α-amylase is defined according to the IUB enzyme nomenclature as EC 3.2.1.1. Alternative Name(s):1,4-ALPHA-D-GLUCAN GLUCANOHYDROLASE, GLYCOGENASE. Reaction catalysed: ENDOHYDROLYSIS OF 1,4-ALPHA-GLUCOSIDIC LINKAGES IN OLIGOSACCHARIDES AND POLYASACCHARIDES.

"amylolytic" In the present context, the term "amylolytic" or "amylolytic activity" is intended to indicate that the enzyme in question has a starch-degrading capability. Specific examples of enzymes having amylolytic activity, i.e. amylolytic enzymes, includes α-amylases, pullulanases, neo-pullulanases, iso-amylases, beta-amylases, CTGases, maltogenases as well as G-4 and G-6 amylases.

"moderate thermo alkaliphile": The term "moderately thermo alkaliphile" relates to a cell which is capable of surviving at relatively high temperatures, i.e. at a temperature above.55° C. such as above 60° C. or 65° C., and at relatively high pH levels, above 8.5 such as above 9 or 10.

"extracellular": The term "extracellular" as used herein in connection with an enzyme relates to an enzyme which is exported out of the cell producing the enzyme, i.e. it is secreted by or diffused out of the cell. Such an enzyme will generally comprise a signal-peptide to guide the secretion (i.e. exporting out of the cell) of the enzyme.

DETAILED DESCRIPTION OF THE INVENTION

Amylase obtained from *Thermoalcalibacter bogoriae*:

The effect of metal ions on the activity of the amylase of the present invention was examined by pre-incubating the enzyme together with metal ions for 30 min. at 65° C., pH 8.0 in a substrate solution containing (wt/vol) soluble starch (0.5%). Subsequently an enzyme assay was performed at 65° C. for 30 min in order to determine the residual activity of the amylase. For further details see working example herein (vide infra) and FIG. 4.

Using this method the amylase of the present invention is preferably having at least 65% of residual amylase activity with a $Ca^{2+}$ concentration between 0.5 mM to 6 mM $Ca^{2+}$, more preferably having at least 65% of residual activity with a $Ca^{2+}$ concentration between 1.0 mM to 5 mM $Ca^{2+}$, and even more preferably having at least 65% of residual amylase activity with a $Ca^{2+}$ concentration between 2 mM to 4 mM $Ca^{2+}$.

In a further embodiment, the α-amylase of the invention is preferably one which has a molecular mass of 57±10 kDA, more preferably a molecular mass of 57±5 kDA, even more preferably a molecular mass of 57±3 kDA, and most preferably a molecular mass of 57±2 kDA.

The molecular mass is measured by SDS-PAGE electrophoresis as further described in the "Materials and Methods" section (vide infra).

In a further embodiment, the α-amylase of the invention is preferably one which has a temperature optimum of 65±10° C., more preferably a temperature optimum of 65±5° C., and even more preferably a temperature optimum of 65±2° C.

The temperature optimum is measured by incubating the enzyme with a 0.5% (wt/vol) substrate solution (soluble starch; Merck) in 100 mM sodium phosphate buffer at pH 9.0. Incubation was done for 30 min. at temperatures between 30–80° C. For further details see working example herein (vide infra).

In a further embodiment, the α-amylase of the invention is preferably one which has a pH optimum in the range between pH 8 to pH 10, more preferably in the range between pH 8.5 to pH 9.5.

The pH optimum is measured by incubating the enzyme with a 0.5% (wt/vol) substrate solution (soluble starch; Merck) in a 120 mM universal Britton Robinsson buffer. For further details see working example herein (vide infra).

Cloning of amylase:

Without being limited to any theory it is at present contemplated that an DNA sequence encoding an amylase of the present invention can be cloned from a strain of *Thermoalcalibacter bogoriae*.

A number of suitable standard DNA cloning methods are e.g. described by Sambrook et al. (Molecular Cloning: A Laboratory Manual. Cold Spring Harbor Lab.; Cold Spring Harbor, N.Y. (1989)).

The DNA sequence may be cloned by purifying the enzyme (e.g. as described in a working example herein (vide infra)), amino acid sequencing, and preparing a suitable probe or PCR primer based on this amino acid sequence.

The DNA sequence the invention can also be cloned by any general method involving cloning, in suitable vectors, a DNA library from any organism expected to produce the amylase of interest, transforming suitable host cells with said vectors, culturing the host cells under suitable conditions to express any enzyme of interest encoded by a clone in the DNA library, screening for positive clones by determining any amylase activity of the enzyme produced by such clones, and isolating the enzyme encoding DNA from such clones.

Microbial Sources

The α-amylase of the invention may be obtained from bacteria corresponding to the Thermoalcalibacter line within the Clostridium/Bacillus subphyllum in particular a strain of *Thermoalcalibacter bogoriae* as described below:

Characteristic of *Thermoalcalibacter bogoriae*

Cells are rod-shaped, 0.3–0.5 mm thick and 3–5 mm long. Colonies are 3–5 mm in diameter, pale-whitish, lense-shaped. Obligately anaerobic. Temperature range for growth from 30° C. to 65° C., optimum around 50° C. to 55° C. Range of growth from pH 6 to 10.5, optimum at pH 9.5; growth from 0 to 4 % NaCl with an optimum around 1% NaCl, represents an optimum $Na^+$ concentration of 230 mM. Grows heterotrophically with peptone. Growth in presence of sulfate, thiosulfate or sulfur. Thiosulfate enhances growth on a fermentable substrate such as glucose and starch, resulting in the formation of $H_2S$. Fermentation products on starch with thiosulfate are acetate and ethanol. Cell wall type is Gram-positive, but cell wall is atypically thin. Sheat like structures at the cell separation area. Branched cells were regularly present. Parts of an outer surface layer were observed.

16S rRNA analysis shows that *Thermoalcalibacter bogoriae* represents a new line within the Clostridium/Bacillus subphyllum. The 16 rRNA sequencing analysis was done at Deutche Sammlung von Mikroorganismen und Zellkulturen (DSMZ).

An isolate of a strain of *Thermoalcalibacter bogoriae* from which an α-amylase of the invention can be derived has been deposited by the inventors according to the Budapest Treaty on the International Recognition of the Deposit of Microorganisms for the Purposes of Patent Procedure at the Deutche Sammlung von Mikroorganismen und Zellkulturen, Mascheroder Weg 1b, D-38124 Braunschweig, Federal Republic of Germany, (DSMZ).

Deposit date : 11 of Sep. 1996

Depositor's ref. : NN049260

DSM No. *Thermoalcalibacter bogoriae* DSM No. 9380.

Method of producing amylase

The amylase of the present invention may be produced by cultivation of a homologous strain e.g. the above mentioned deposited strain in a suitable medium resulting in conditions permitting the production of the enzyme. The medium used to culture the strain may be any conventional medium suitable for growing the cells in question. The secreted, into the culture medium, amylase may be recovered therefrom by well-known procedures including separating the cells from the medium by centrifugation or filtration, precipitating proteinaceous components of the medium by means of a salt such as ammonium sulphate, followed by chromatographic procedures such as ion exchange chromatography, affinity chromatography, or the like.

Enzyme compositions

In a still further aspect, the present invention relates to an enzyme composition, which comprises an amylase as described above.

The enzyme composition of the invention may contain one or more other enzymes, for instance proteases, lipases, amylolytic enzymes, oxidases (including peroxidases), or cellulases (mentioned examples are examples preferably for use in odetergents), e.g. Savinase®, Durazyme®, Esperase®, Alcalase®, Termamyl® or Celluzyme™ (all available from Novo Nordisk A/S)").

The enzyme composition may be prepared in accordance with methods known in the art and may be in the form of a liquid or a dry composition. For instance, the enzyme composition may be in the form of a granulate or a microgranulate (U.S. Pat. No. 4,106,991, U.S. Pat. No. 5,324,649). The enzyme to be included in the composition may be stabilized in accordance with methods known in the art.

Examples are given below of preferred uses of the enzyme composition of the invention. The dosage of the enzyme composition of the invention and other conditions under which the composition is used may be determined on the basis of methods known in the art.

The enzyme and/or the enzyme composition according to the invention may be useful for at least one of the following purposes.

Applications of the amylase of the present invention:

The amylase enzyme of the invention may be used in conventional applications of amylase enzyme, particularly at conditions where only low concentration of $Ca^{2+}$ are present, e.g. in laundry and dishwash detergents, in institutional and industrial cleaning.

The amylase enzymes of the invention can also be used for starch liquefaction, textile desizing, starch modification in the paper and pulp industry, and for brewing and baking.

DETERGENT DISCLOSURE AND EXAMPLES

Surfactant system

The detergent compositions according to the present invention comprise a surfactant system, wherein the surfactant can be selected from nonionic and/or anionic and/or cationic and/or ampholytic and/or zwitterionic and/or semipolar surfactants.

The surfactant is typically present at a level from 0.1% to 60% by weight.

The surfactant is preferably formulated to be compatible with enzyme components present in the composition. In liquid or gel compositions the surfactant is most preferably formulated in such a way that it promotes, or at least does not degrade, the stability of any enzyme in these compositions.

Preferred systems to be used according to the present invention comprise as a surfactant one or more of the nonionic and/or anionic surfactants described herein.

Polyethylene, polypropylene, and polybutylene oxide condensates of alkyl phenols are suitable for use as the nonionic surfactant of the surfactant systems of the present invention, with the polyethylene oxide condensates being preferred. These compounds include the condensation products of alkyl phenols having an alkyl group containing from about 6 to about 14 carbon atoms, preferably from about 8 to about 14 carbon atoms, in either a straight chain or branched-chain configuration with the alkylene oxide. In a preferred embodiment, the ethylene oxide is present in an amount equal to from about 2 to about 25 moles, more preferably from about 3 to about 15 moles, of ethylene oxide per mole of alkyl phenol. Commercially available nonionic surfactants of this type include Igepal™ CO-630, marketed by the GAF Corporation; and Triton™ X-45, X-114, X-100 and X-102, all marketed by the Rohm & Haas Company. These surfactants are commonly referred to as alkylphenol alkoxylates (e.g., alkyl phenol ethoxylates).

The condensation products of primary and secondary aliphatic alcohols with about 1 to about 25 moles of ethylene oxide are suitable for use as the nonionic surfactant of the nonionic surfactant systems of the present invention. The alkyl chain of the aliphatic alcohol can either be straight or branched, primary or secondary, and generally contains from about 8 to about 22 carbon atoms. Preferred are the condensation products of alcohols having an alkyl group containing from about 8 to about 20 carbon atoms, more preferably from about 10 to about 18 carbon atoms, with from about 2 to about 10 moles of ethylene oxide per mole of alcohol. About 2 to about 7 moles of ethylene oxide and most preferably from 2 to 5 moles of ethylene oxide per mole of alcohol are present in said condensation products. Examples of commercially available nonionic surfactants of this type include Tergitol™ 15-S-9 (The condensation product of $C_{11}$–$C_{15}$ linear alcohol with 9 moles ethylene oxide), Tergitolt™ 24-L-6 NMW (the condensation product of $C_{12}$–$C_{14}$ primary alcohol with 6 moles ethylene oxide with a narrow molecular weight distribution), both marketed by Union Carbide Corporation; Neodol™ 45-9 (the condensation product of $C_{14}$–$C_{15}$ linear alcohol with 9 moles of ethylene oxide), Neodol™ 23-3 (the condensation product of $C_{12}$–$C_{13}$ linear alcohol with 3.0 moles of ethylene oxide), Neodol™ 45-7 (the condensation product of $C_{14}$–$C_{15}$ linear alcohol with 7 moles of ethylene oxide), Neodol™ 45-5 (the condensation product of $C_{14}$–$C_{15}$ linear alcohol with 5 moles of ethylene oxide) marketed by Shell Chemical Company, Kyro™ EOB (the condensation product of $C_{13}$–$C_{15}$ alcohol with 9 moles ethylene oxide), marketed by The Procter & Gamble Company, and Genapol LA 050 (the condensation product of $C_{12}$–$C_{14}$ alcohol with 5 moles of ethylene oxide) marketed by Hoechst. Preferred range of HLB in these products is from 8–11 and most preferred from 8–10.

Also useful as the nonionic surfactant of the surfactant systems of the present invention are alkylpolysaccharides disclosed in U.S. Pat. No. 4,565,647, having a hydrophobic group containing from about 6 to about 30 carbon atoms, preferably from about 10 to about 16 carbon atoms and a polysaccharide, e.g. a polyglycoside, hydrophilic group containing from about 1.3 to about 10, preferably from about 1.3 to about 3, most preferably from about 1.3 to about 2.7 saccharide units. Any reducing saccharide containing 5 or 6 carbon atoms can be used, e.g., glucose, galactose and galactosyl moieties can be substituted for the glucosyl moieties (optionally the hydrophobic group is attached at the 2-, 3-, 4-, etc. positions thus giving a glucose or galactose as opposed to a glucoside or galactoside). The intersaccharide bonds can be, e.g., between the one position of the additional saccharide units and the 2-, 3-, 4-, and/or 6- positions on the preceding saccharide units.

The preferred alkylpolyglycosides have the formula

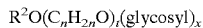

wherein $R^2$ is selected from the group consisting of alkyl, alkylphenyl, hydroxyalkyl, hydroxyalkylphenyl, and mixtures thereof in which the alkyl groups contain from about 10 to about 18, preferably from about 12 to about 14, carbon atoms; n is 2 or 3, preferably 2; t is from 0 to about 10, preferably 0; and x is from about 1.3 to about 10, preferably from about 1.3 to about 3, most preferably from about 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4-, and/or 6-position, preferably predominantly the 2-position.

The condensation products of ethylene oxide with a hydrophobic base formed by the condensation of propylene oxide with propylene glycol are also suitable for use as the additional nonionic surfactant systems of the present invention. The hydrophobic portion of these compounds will preferably have a molecular weight from about 1500 to about 1800 and will exhibit water insolubility. The addition of polyoxyethylene moieties to this hydrophobic portion tends to increase the water solubility of the molecule as a whole, and the liquid character of the product is retained up to the point where the polyoxyethylene content is about 50% of the total weight of the condensation product, which corresponds to condensation with up to about 40 moles of ethylene oxide. Examples of compounds of this type include certain of the commercially available Pluronic™ surfactants, marketed by BASF.

Also suitable for use as the nonionic surfactant of the nonionic surfactant system of the present invention, are the condensation products of ethylene oxide with the product resulting from the reaction of propylene oxide and ethylenediamine. The hydrophobic moiety of these products consists of the reaction product of ethylenediamine and excess propylene oxide, and generally has a molecular weight of from about 2500 to about 3000. This hydrophobic moiety is condensed with ethylene oxide to the extent that the condensation product contains from about 40% to about 80% by weight of polyoxyethylene and has a molecular weight of from about 5,000 to about 11.000. Examples of this type of nonionic surfactant include certain of the commercially available Tetronic™ compounds, marketed by BASF.

Preferred for use as the nonionic surfactant of the surfactant systems of the present invention are polyethylene oxide condensates of alkyl phenols, condensation products of primary and secondary aliphatic alcohols with from about 1 to about 25 moles of ethyleneoxide, alkylpolysaccharides, and mixtures hereof. Most preferred are $C_8$–$C_{14}$ alkyl phenol ethoxylates having from 3 to 15 ethoxy groups and $C_8$–$C_{18}$ alcohol ethoxylates (preferably $C_{10}$ avg.) having from 2 to 10 ethoxy groups, and mixtures thereof.

Highly preferred nonionic surfactants are polyhydroxy fatty acid amide surfactants of the formula

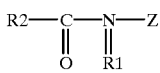

wherein $R^1$ is H, or $R^1$ is $C_{1-4}$ hydrocarbyl, 2-hydroxyethyl, 2-hydroxypropyl or a mixture thereof, $R^2$ is $C_{5-31}$ hydrocarbyl, and Z is a polyhydroxyhydrocarbyl having a linear hydrocarbyl chain with at least 3 hydroxyls directly connected to the chain, or an alkoxylated derivative thereof. Preferably, $R^1$ is methyl, $R^2$ is straight $C_{11-15}$ alkyl or $C_{16-18}$, alkyl or alkenyl chain such as coconut alkyl or mixtures thereof, and Z is derived from a reducing sugar such as glucose, fructose, maltose or lactose, in a reductive amination reaction.

Highly preferred anionic surfactants include alkyl alkoxylated sulfate surfactants. Examples hereof are water soluble salts or acids of the formula $RO(A)_mSO3M$ wherein R is an unsubstituted $C_{10}$–$C_{24}$ alkyl or hydroxyalkyl group having a $C_{10}$–$C_{24}$ alkyl component, preferably a $C_{12}$–$C_{20}$ alkyl or hydroxyalkyl, more preferably $C_{12}$–$C_{18}$ alkyl or hydroxyalkyl, A is an ethoxy or propoxy unit, m is greater than zero, typically between about 0.5 and about 6, more preferably between about 0.5 and about 3, and M is H or a cation which can be, for example, a metal cation (e.g., sodium, potassium, lithium, calcium, magnesium, etc.), ammonium or substituted-ammonium cation. Alkyl ethoxylated sulfates as well as alkyl propoxylated sulfates are contemplated herein. Specific examples of substituted ammonium cations include methyl-, dimethyl, trimethyl-ammonium cations and quaternary ammonium cations such as tetramethyl-ammonium and dimethyl piperdinium cations and those derived from alkylamines such as ethylamine, diethylamine, triethylamine, mixtures thereof, and the like. Exemplary surfactants are $C_{12}$–$C_{18}$ alkyl polyethoxylate (1.0) sulfate ($C_{12}$–$C_{18}$E (1.0) M), $C_{12}$–$C_{18}$ alkyl polyethoxylate (2.25) sulfate ($C_{12}$–$C_{18}$(2.25)M, and $C_{12}$–$C_{18}$ alkyl polyethoxylate (3.0) sulfate ($C_{12}$–$C_{18}$E(3.0)M), and $C_{12}$–$C_{18}$ alkyl polyethoxylate (4.0) sulfate ($C_{12}$–$C_{18}$E(4.0) M), wherein M is conveniently selected from sodium and potassium.

Suitable anionic surfactants to be used are alkyl ester sulfonate surfactants including linear esters of $C_8$–$C_{20}$ carboxylic acids (i.e., fatty acids) which are sulfonated with gaseous $SO_3$ according to "The Journal of the American Oil Chemists Society", 52 (1975), pp. 323–329. Suitable starting materials would include natural fatty substances as derived from tallow, palm oil, etc.

The preferred alkyl ester sulfonate surfactant, especially for laundry applications, comprise alkyl ester sulfonate surfactants of the structural formula:

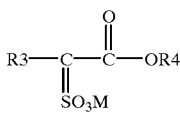

wherein $R^3$ is a $C_8$–$C_{20}$ hydrocarbyl, preferably an alkyl, or combination thereof, $R^4$ is a $C_1$–$C_6$ hydrocarbyl, preferably an alkyl, or combination thereof, and M is a cation which forms a water soluble salt with the alkyl ester sulfonate. Suitable salt-forming cations include metals such as sodium, potassium, and lithium, and substituted or unsubstituted ammonium cations, such as monoethanolamine, diethonolamine, and triethanolamine. Preferably, $R^3$ is $C_{10}$–$C_{16}$ alkyl, and $R^4$ is methyl, ethyl or isopropyl. Especially preferred are the methyl ester sulfonates wherein $R^3$ is $C_{10}$–$C_{16}$ alkyl.

Other suitable anionic surfactants include the alkyl sulfate surfactants which are water soluble salts or acids of the formula ROSO$_3$M wherein R preferably is a C$_{10}$–C$_{24}$ hydrocarbyl, preferably an alkyl or hydroxyalkyl having a C$_{10}$–C$_{20}$ alkyl component, more preferably a C$_{12}$–C$_{18}$ alkyl or hydroxyalkyl, and M is H or a cation, e.g., an alkali metal cation (e.g. sodium, potassium, lithium), or ammonium or substituted ammonium (e.g. methyl-, dimethyl-, and trimethyl ammonium cations and quaternary ammonium cations such as tetramethyl-ammonium and dimethyl piperdinium cations and quaternary ammonium cations derived from alkylamines such as ethylamine, diethylamine, triethylamine, and mixtures thereof, and the like). Typically, alkyl chains of C$_{12}$–C$_{16}$ are preferred for lower wash temperatures (e.g. below about 50° C.) and C$_{16}$–C$_{18}$ alkyl chains are preferred for higher wash temperatures (e.g. above about 50° C.).

Other anionic surfactants useful for detersive purposes can also be included in the laundry detergent compositions of the present invention. Theses can include salts (including, for example, sodium, potassium, ammonium, and substituted ammonium salts such as mono- di- and triethanolamine salts) of soap, C$_8$–C$_{22}$ primary or secondary alkanesulfonates, C$_8$–C$_{24}$ olefinsulfonates, sulfonated polycarboxylic acids prepared by sulfonation of the pyrolyzed product of alkaline earth metal citrates, e.g., as described in British patent specification No. 1,082,179, C$_8$–C$_{24}$ alkylpolyglycolethersulfates (containing up to 10 moles of ethylene oxide); alkyl glycerol sulfonates, fatty acyl glycerol sulfonates, fatty oleyl glycerol sulfates, alkyl phenol ethylene oxide ether sulfates, paraffin sulfonates, alkyl phosphates, isethionates such as the acyl isethionates, N-acyl taurates, alkyl succinamates and sulfosuccinates, monoesters of sulfosuccinates (especially saturated and unsaturated C$_{12}$–C$_{18}$ monoesters) and diesters of sulfosuccinates (especially saturated and unsaturated C$_6$–C$_{12}$ diesters), acyl sarcosinates, sulfates of alkylpolysaccharides such as the sulfates of alkylpolyglucoside (the nonionic nonsulfated compounds being described below), branched primary alkyl sulfates, and alkyl polyethoxy carboxylates such as those of the formula RO(CH$_2$CH$_2$O)$_k$-CH$_2$COO-M+ wherein R is a C$_8$–C$_{22}$ alkyl, k is an integer from 1 to 10, and M is a soluble salt forming cation. Resin acids and hydrogenated resin acids are also suitable, such as rosin, hydrogenated rosin, and resin acids and hydrogenated resin acids present in or derived from tall oil.

Alkylbenzene sulfonates are highly preferred. Especially preferred are linear (straight-chain) alkyl benzene sulfonates (LAS) wherein the alkyl group preferably contains from 10 to 18 carbon atoms.

Further examples are described in "Surface Active Agents and Detergents" (Vol. I and II by Schwartz, Perrry and Berch). A variety of such surfactants are also generally disclosed in U.S. Pat. No. 3,929,678, (Column 23, line 58 through Column 29, line 23, herein incorporated by reference).

When included therein, the laundry detergent compositions of the present invention typically comprise from about 1% to about 40%, preferably from about 3% to about 20% by weight of such anionic surfactants.

The laundry detergent compositions of the present invention may also contain cationic, ampholytic, zwitterionic, and semi-polar surfactants, as well as the nonionic and/or anionic surfactants other than those already described herein.

Cationic detersive surfactants suitable for use in the laundry detergent compositions of the present invention are those having one long-chain hydrocarbyl group. Examples of such cationic surfactants include the ammonium surfactants such as alkyltrimethylammonium halogenides, and those surfactants having the formula:

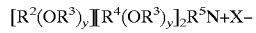

wherein R$^2$ is an alkyl or alkyl benzyl group having from about 8 to about 18 carbon atoms in the alkyl chain, each R$^3$ is selected form the group consisting of —CH$_2$CH$_2$—, —CH$_2$CH(CH$_3$)—, —CH$_2$CH(CH$_2$OH)—, —CH$_2$CH$_2$CH$_2$—, and mixtures thereof; each R$^3$ is selected from the group consisting of C$_1$–C$_4$ alkyl, C$_1$–C$_4$ hydroxyalkyl, benzyl ring structures formed by joining the two R$^4$ groups, —CH$_2$CHOHCHOHCOR$^6$CHOHCH$_2$OH, wherein R$^6$ is any hexose or hexose polymer having a molecular weight less than about 1000, and hydrogen when y is not 0; R$^5$ is the same as R or is an alkyl chain, wherein the total number of carbon atoms or R$^2$ plus R$^5$ is not more than about 18; each y is from 0 to about 10, and the sum of the y values is from 0 to about 15; and X is any compatible anion.

Highly preferred cationic surfactants are the water soluble quaternary ammonium compounds useful in the present composition having the formula:

$$R_1R_2R_3R_4N^+X^- \qquad (i)$$

wherein R$_1$ is C$_8$–C$_{16}$ alkyl, each of R$_2$, R$_3$ and R$_4$ is independently C$_1$–C$_4$ alkyl, C$_1$–C$_4$ hydroxy alkyl, benzyl, and —(C$_2$H$_{40}$)$_x$H where x has a value from 2 to 5, and X is an anion. Not more than one of R$_2$, R$_3$ or R$_4$ should be benzyl.

The preferred alkyl chain length for R$_1$ is C$_{12}$–C$_{15}$, particularly where the alkyl group is a mixture of chain lengths derived from coconut or palm kernel fat or is derived synthetically by olefin build up or OXO alcohols synthesis.

Preferred groups for R$_2$R$_3$ and R$_4$ are methyl and hydroxyethyl groups and the anion X may be selected from halide, methosulphate, acetate and phosphate ions. Examples of suitable quaternary ammonium compounds of formulae (i) for use herein are:

coconut trimethyl ammonium chloride or bromide;

coconut methyl dihydroxyethyl ammonium chloride or bromide;

decyl triethyl ammonium chloride;

decyl dimethyl hydroxyethyl ammonium chloride or bromide;

C$_{12-15}$ dimethyl hydroxyethyl ammonium chloride or bromide;

coconut dimethyl hydroxyethyl ammonium chloride or bromide;

myristyl trimethyl ammonium methyl sulphate;

lauryl dimethyl benzyl ammonium chloride or bromide;

lauryl dimethyl (ethenoxy)$_4$ ammonium chloride or bromide;

choline esters (compounds of formula (i) wherein R1 is

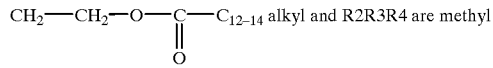

di-alkyl imidazolines [compounds of formula (i)].

Other cationic surfactants useful herein are also described in U.S. Pat. No. 4,228,044 and in EP 000 224.

When included therein, the laundry detergent compositions of the present invention typically comprise from 0.2% to about 25%, preferably from about 1% to about 8% by weight of such cationic surfactants.

Ampholytic surfactants are also suitable for use in the laundry detergent compositions of the present invention. These surfactants can be broadly described as aliphatic derivatives of secondary or tertiary amines, or aliphatic derivatives of heterocyclic secondary and tertiary amines in which the aliphatic radical can be straight- or branched-chain. One of the aliphatic substituents contains at least about 8 carbon atoms, typically from about 8 to about 18 carbon atoms, and at least one contains an anionic water-solubilizing group, e.g. carboxy, sulfonate, sulfate. See U.S. Pat. No. 3,929,678 (column 19, lines 18–35) for examples of ampholytic surfactants.

When included therein, the laundry detergent compositions of the present invention typically comprise from 0.2% to about 15%, preferably from about 1% to about 10% by weight of such ampholytic surfactants.

Zwitterionic surfactants are also suitable for use in laundry detergent compositions. These surfactants can be broadly described as derivatives of secondary and tertiary amines, derivatives of heterocyclic secondary and tertiary amines, or derivatives of quaternary ammonium, quaternary phosphonium or tertiary sulfonium compounds. See U.S. Pat. No. 3,929,678 (column 19, line 38 through column 22, line 48) for examples of zwitterionic surfactants.

When included therein, the laundry detergent compositions of the present invention typically comprise from 0.2% to about 15%, preferably from about 1% to about 10% by weight of such zwitterionic surfactants.

Semi-polar nonionic surfactants are a special category of nonionic surfactants which include water-soluble amine oxides containing one alkyl moiety of from about 10 to about 18 carbon atoms and 2 moieties selected from the group consisting of alkyl groups and hydroxyalkyl groups containing from about 1 to about 3 carbon atoms; water-soluble phosphine oxides containing one alkyl moiety of form about 10 to about 18 carbon atoms and 2 moieties selected from the group consisting of alkyl groups and hydroxyalkyl groups containing from about 1 to about 3 carbon atoms; and water-soluble sulfoxides containing one alkyl moiety from about 10 to about 18 carbon atoms and a moiety selected from the group consisting of alkyl and hydroxyalkyl moieties of from about 1 to about 3 carbon atoms.

Semi-polar nonionic detergent surfactants include the amine oxide surfactants having the formula:

wherein $R^3$ is an alkyl, hydroxyalkyl, or alkyl phenyl group or mixtures thereof containing from about 8 to about 22 carbon atoms; $R^4$ is an alkylene or hydroxyalkylene group containing from about 2 to about 3 carbon atoms or mixtures thereof; x is from 0 to about 3: and each $R^5$ is an alkyl or hydroxyalkyl group containing from about 1 to about 3 carbon atoms or a polyethylene oxide group containing from about 1 to about 3 ethylene oxide groups. The $R^5$ groups can be attached to each other, e.g., through an oxygen or nitrogen atom, to form a ring structure.

These amine oxide surfactants in particular include $C_{10}$–$C_{18}$ alkyl dimethyl amine oxides and $C_8$–$C_{12}$ alkoxy ethyl dihydroxy ethyl amine oxides.

When included therein, the laundry detergent compositions of the present invention typically comprise from 0.2% to about 15%, preferably from about 1% to about 10% by weight of such semi-polar nonionic surfactants.

Builder system

The compositions according to the present invention may further comprise a builder system. Any conventional builder system is suitable for use herein including aluminosilicate materials, silicates, polycarboxylates and fatty acids, materials such as ethylenediamine tetraacetate, metal ion sequestrants such as aminopolyphosphonates, particularly ethylenediamine tetramethylene phosphonic acid and diethylene triamine pentamethylenephosphonic acid. Though less preferred for obvious environmental reasons, phosphate builders can also be used herein.

Suitable builders can be an inorganic ion exchange material, commonly an inorganic hydrated aluminosilicate material, more particularly a hydrated synthetic zeolite such as hydrated zeolite A, X, B, HS or MAP.

Another suitable inorganic builder material is layered silicate, e.g. SKS-6 (Hoechst). SKS-6 is a crystalline layered silicate consisting of sodium silicate ($Na_2Si_2O_5$).

Suitable polycarboxylates containing one carboxy group include lactic acid, glycolic acid and ether derivatives thereof as disclosed in Belgian Patent Nos. 831,368, 821,369 and 821,370. Polycarboxylates containing two carboxy groups include the water-soluble salts of succinic acid, malonic acid, (ethylenedioxy) diacetic acid, maleic acid, diglycollic acid, tartaric acid, tartronic acid and fumaric acid, as well as the ether carboxylates described in German Offenle-enschrift 2,446,686, and 2,446,487, U.S. Pat. No. 3,935,257 and the sulfinyl carboxylates described in Belgian Patent No. 840,623. Polycarboxylates containing three carboxy groups include, in particular, water-soluble citrates, aconitrates and citraconates as well as succinate derivatives such as the carboxymethyloxysuccinates described in British Patent No. 1,379,241, lactoxysuccinates described in Netherlands Application 7205873, and the oxypolycarboxylate materials such as 2-oxa-1,1,3-propane tricarboxylates described in British Patent No. 1,387,447.

Polycarboxylates containing four carboxy groups include oxydisuccinates disclosed in British Patent No. 1,261,829, 1,1,2,2,-ethane tetracarboxylates, 1,1,3,3-propane tetracarboxylates containing sulfo substituents include the sultosuccinate derivatives disclosed in British Patent Nos. 1,398,421 and 1,398,422 and in U.S. Pat. No. 3,936,448, and the sulfonated pyrolysed citrates described in British Patent No. 1,082,179, while polycarboxylates containing phosphone substituents are disclosed in British Patent No. 1,439,000.

Alicyclic and heterocyclic polycarboxylates include cyclopentane-cis,cis-cis-tetracarboxylates, cyclopentadienide pentacarboxylates, 2,3,4,5-tetrahydro-furan - cis, cis, cis-tetracarboxylates, 2,5-tetrahydro-furan-cis, discarboxylates, 2,2,5,5,-tetrahydrofuran - tetracarboxylates, 1,2,3,4,5,6-hexane - hexacarboxylates and carboxymethyl derivatives of polyhydric alcohols such as sorbitol, mannitol and xylitol. Aromatic polycarboxylates include mellitic acid, pyromellitic acid and the phthalic acid derivatives disclosed in British Patent No. 1,425,343.

Of the above, the preferred polycarboxylates are hydroxycarboxylates containing up to three carboxy groups per molecule, more particularly citrates.

Preferred builder systems for use in the present compositions include a mixture of a water-insoluble aluminosilicate builder such as zeolite A or of a layered silicate (SKS-6), and a water-soluble carboxylate chelating agent such as citric acid.

A suitable chelant for inclusion in the detergent compositions in accordance with the invention is ethylenediamine-N,N'-disuccinic acid (EDDS) or the alkali metal, alkaline earth metal, ammonium, or substituted ammonium salts thereof, or mixtures thereof. Preferred EDDS compounds are the free acid form and the sodium or magnesium salt thereof. Examples of such preferred sodium salts of EDDS include $Na_2EDDS$ and $Na_4EDDS$. Examples of such preferred magnesium salts of EDDS include MgEDDS and $Mg_2EDDS$. The magnesium salts are the most preferred for inclusion in compositions in accordance with the invention.

Preferred builder systems include a mixture of a water-insoluble aluminosilicate builder such as zeolite A, and a water soluble carboxylate chelating agent such as citric acid.

Other builder materials that can form part of the builder system for use in granular compositions include inorganic materials such as alkali metal carbonates, bicarbonates, silicates, and organic materials such as the organic phosphonates, amino polyalkylene phosphonates and amino polycarboxylates.

Other suitable water-soluble organic salts are the homo- or co-polymeric acids or their salts, in which the polycarboxylic acid comprises at least two carboxyl radicals separated form each other by not more than two carbon atoms.

Polymers of this type are disclosed in GB-A-1,596,756. Examples of such salts are polyacrylates of MW 2000–5000 and their copolymers with maleic anhydride, such copolymers having a molecular weight of from 20,000 to 70,000, especially about 40,000.

Detergency builder salts are normally included in amounts of from 5% to 80% by weight of the composition. Preferred levels of builder for liquid detergents are from 5% to 30%.

Enzymes

Preferred detergent compositions, in addition to the enzyme preparation of the invention, comprise other enzyme (s) which provides cleaning performance and/or fabric care benefits.

Such enzymes include proteases, other lipases, cutinases, amylases, cellulases, peroxidases, oxidases (e.g. laccases).

Proteases: Any protease suitable for use in alkaline solutions can be used. Suitable proteases include those of animal, vegetable or microbial origin. Microbial origin is preferred. Chemically or genetically modified mutants are included. The protease may be a serine protease, preferably an alkaline microbial protease or a trypsin-like protease. Examples of alkaline proteases are subtilisins, especially those derived from Bacillus, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the Fusarium protease described in WO 89/06270.

Preferred commercially available protease enzymes include those sold under the trade names Alcalase, Savinase, Primase, Durazym, and Esperase by Novo Nordisk A/S (Denmark), those sold under the tradename Maxatase, Maxacal, Maxapem and Properase by Gist-Brocades, those sold under the tradename Purafect and Purafect OXP by Genencor International, and those sold under the tradename Opticlean and Optimase by Solvay Enzymes. Protease enzymes may be incorporated into the compositions in accordance with the invention at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Lipases: Any lipase suitable for use in alkaline solutions can be used. Suitable lipases include those of bacterial or fungal origin. Chemically or genetically modified mutants are included.

Examples of useful lipases include a *Humicola lanuginosa* lipase, e.g., as described in EP 258 068 and EP 305 216, a *Rhizomucor miehei* lipase, e.g., as described in EP 238 023, a Candida lipase, such as a *C. antarctica* lipase, e.g., the *C. antarctica* lipase A or B described in EP 214 761, a *Pseudomonas lipase* such as a *P. alcaligenes* and *P. pseudoalcaligenes* lipase, e.g., as described in EP 218 272, a *P. cepacia* lipase, e.g., as described in EP 331 376, a *P. stutzeri* lipase, e.g., as disclosed in GB 1,372,034, a *P. fluorescens* lipase, a *Bacillus lipase*, e.g., a *B. subtilis* lipase (Dartois et al., (1993), Biochemica et Biophysica acta 1131, 253–260), a *B. stearothermophilus* lipase (JP 64/744992) and a *B. pumilus* lipase (WO 91/16422).

Furthermore, a number of cloned lipases may be useful, including the *Penicillium camembertii* lipase described by Yamaguchi et al., (1991), Gene 103, 61–67), the *Geotricum candidum* lipase (Schimada, Y. et al., (1989), J. Biochem., 106, 383–388), and various Rhizopus lipases such as a *R. delemar* lipase (Hass, M. J et al., (1991), Gene 109, 117–113), a *R. niveus* lipase (Kugimiya et al., (1992), Biosci. Biotech. Biochem. 56, 716–719) and a *R. oryzae* lipase.

Other types of lipolytic enzymes such as cutinases may also be useful, e.g., a cutinase derived from *Pseudomonas mendocina* as described in WO 88/09367, or a cutinase derived from *Fusarium solani pisi* (e.g. described in WO 90/09446). Especially suitable lipases are lipases such as M1 Lipase™, Luma fast™ and Lipomax™ (Genencor), Lipolase™ and Lipolase Ultra™ (Novo Nordisk A/S), and Lipase P "Amano" (Amano Pharmaceutical Co. Ltd.).

The lipases are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Amylases: Any amylase ($\alpha$ and/or $\beta$) suitable for use in alkaline solutions can be used. Suitable amylases include those of bacterial or fungal origin. Chemically or genetically modified mutants are included. Amylases include, for example, $\alpha$-amylases obtained from a special strain of *B. licheniformis*, described in more detail in GB 1,296,839. Commercially available amylases are Duramyl™, Termamyl™, Fungamyl™ and BAN™ (available from Novo Nordisk A/S) and Rapidase™ and Maxamyl P™ (available from Genencor).

The amylases are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Cellulases: Any cellulase suitable for use in alkaline solutions can be used. Suitable cellulases include those of bacterial or fungal origin. Chemically or genetically modified mutants are included. Suitable cellulases are disclosed in U.S. Pat. No. 4,435,307, which discloses fungal cellulases produced from *Humicola insolens*. Especially suitable cellulases are the cellulases having colour care benefits. Examples of such cellulases are cellulases described in European patent application No. 0 495 257.

Commercially available cellulases include Celluzyme™ produced by a strain of *Humicola insolens,* (Novo Nordisk A/S), and KAC-500(B)™ (Kao Corporation).

Cellulases are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Peroxidases/Oxidases: Peroxidase enzymes are used in combination with hydrogen peroxide or a source thereof (e.g. a percarbonate, perborate or persulfate). Oxidase enzymes are used in combination with oxygen. Both types of enzymes are used for "solution bleaching", i.e. to prevent transfer of a textile dye from a dyed fabric to another fabric when said fabrics are washed together in a wash liquor, preferably together with an enhancing agent as described in e.g. WO 94/12621 and WO 95/01426. Suitable peroxidases/oxidases include those of plant, bacterial or fungal origin. Chemically or genetically modified mutants are included.

Peroxidase and/or oxidase enzymes are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Mixtures of the above mentioned enzymes are encompassed herein, in particular a mixture of a protease, an amylase, a lipase and/or a cellulase.

The enzyme of the invention, or any other enzyme incorporated in the detergent composition, is normally incorporated in the detergent composition at a level from 0.00001% to 2% of enzyme protein by weight of the composition, preferably at a level from 0.0001% to 1% of enzyme protein by weight of the composition, more preferably at a level from 0.001% to 0.5% of enzyme protein by weight of the composition, even more preferably at a level from 0.01% to 0.2% of enzyme protein by weight of the composition.

Bleaching agents: Additional optional detergent ingredients that can be included in the detergent compositions of the present invention include bleaching agents such as PB1, PB4 and percarbonate with a particle size of 400–800 microns. These bleaching agent components can include one or more oxygen bleaching agents and, depending upon the bleaching agent chosen, one or more bleach activators. When present oxygen bleaching compounds will typically be present at levels of from about 1% to about 25%. In general, bleaching compounds are optional added components in non-liquid formulations, e.g. granular detergents.

The bleaching agent component for use herein can be any of the bleaching agents useful for detergent compositions including oxygen bleaches as well as others known in the art.

The bleaching agent suitable for the present invention can be an activated or non-activated bleaching agent.

One category of oxygen bleaching agent that can be used encompasses percarboxylic acid bleaching agents and salts thereof. Suitable examples of this class of agents include magnesium monoperoxyphthalate hexahydrate, the magnesium salt of meta-chloro perbenzoic acid, 4-nonylamino-4-oxoperoxybutyric acid and diperoxydodecanedioic acid. Such bleaching agents are disclosed in U.S. Pat. No. 4,483,781, U.S. Pat. No. 740,446, EP 0 133 354 and U.S. Pat. No. 4,412,934. Highly preferred bleaching agents also include 6-nonylamino-6-oxoperoxycaproic acid as described in U.S. Pat. No. 4,634,551.

Another category of bleaching agents that can be used encompasses the halogen bleaching agents. Examples of hypohalite bleaching agents, for example, include trichloro isocyanuric acid and the sodium and potassium dichloroisocyanurates and N-chloro and N-bromo alkane sulphonamides. Such materials are normally added at 0.5–10% by weight of the finished product, preferably 1–5% by weight.

The hydrogen peroxide releasing agents can be used in combination with bleach activators such as tetraacetylethylenediamine (TAED), nonanoyloxybenzenesulfonate (NOBS, described in U.S. Pat. No. 4,412,934), 3,5-trimethyl-hexsanoloxybenzenesulfonate (ISONOBS, described in EP 120 591) or pentaacetylglucose (PAG), which are perhydrolyzed to form a peracid as the active bleaching species, leading to improved bleaching effect. In addition, very suitable are the bleach activators C8(6-octanamido-caproyl) oxybenzene-sulfonate, C9(6-nonanamido caproyl) oxybenzenesulfonate and C10 (6-decanamido caproyl) oxybenzenesulfonate or mixtures thereof. Also suitable activators are acylated citrate esters such as disclosed in European Patent Application No. 91870207.7.

Useful bleaching agents, including peroxyacids and bleaching systems comprising bleach activators and peroxygen bleaching compounds for use in cleaning compositions according to the invention are described in application U.S. Ser. No. 08/136,626.

The hydrogen peroxide may also be present by adding an enzymatic system (i.e. an enzyme and a substrate therefore) which is capable of generation of hydrogen peroxide at the beginning or during the washing and/or rinsing process. Such enzymatic systems are disclosed in European Patent Application EP 0 537 381.

Bleaching agents other than oxygen bleaching agents are also known in the art and can be utilized herein. One type of non-oxygen bleaching agent of particular interest includes photoactivated bleaching agents such as the sulfonated zinc and/or aluminium phthalocyanines. These materials can be deposited upon the substrate during the washing process. Upon irradiation with light, in the presence of oxygen, such as by hanging clothes out to dry in the daylight, the sulfonated zinc phthalocyanine is activated and, consequently, the substrate is bleached. Preferred zinc phthalocyanine and a photoactivated bleaching process are described in U.S. Pat. No. 4,033,718. Typically, detergent composition will contain about 0.025% to about 1.25%, by weight, of sulfonated zinc phthalocyanine.

Bleaching agents may also comprise a manganese catalyst. The manganese catalyst may, e.g., be one of the compounds described in "Efficient manganese catalysts for low-temperature bleaching", *Nature* 369, 1994, pp. 637–639.

Suds suppressors: Another optional ingredient is a suds suppressor, exemplified by silicones, and silica-silicone mixtures. Silicones can generally be represented by alkylated polysiloxane materials, while silica is normally used in finely divided forms exemplified by silica aerogels and xerogels and hydrophobic silicas of various types. Theses materials can be incorporated as particulates, in which the suds suppressor is advantageously releasably incorporated in a water-soluble or waterdispersible, substantially non surface-active detergent impermeable carrier. Alternatively the suds suppressor can be dissolved or dispersed in a liquid carrier and applied by spraying on to one or more of the other components.

A preferred silicone suds controlling agent is disclosed in U.S. Pat. No. 3,933,672. Other particularly useful suds suppressors are the self-emulsifying silicone suds suppressors, described in German Patent Application DTOS 2,646,126. An example of such a compound is DC-544, commercially available form Dow Corning, which is a siloxane-glycol copolymer. Especially preferred suds controlling agent are the suds suppressor system comprising a mixture of silicone oils and 2-alkyl-alkanols. Suitable 2-alkyl-alkanols are 2-butyl-octanol which are commercially available under the trade name Isofol 12 R.

Such suds suppressor system are described in European Patent Application EP 0 593 841.

Especially preferred silicone suds controlling agents are described in European Patent Application No. 92201649.8. Said compositions can comprise a silicone/silica mixture in combination with fumed nonporous silica such as Aerosil®.

The suds suppressors described above are normally employed at levels of from 0.001% to 2% by weight of the composition, preferably from 0.01% to 1% by weight.

Other components: Other components used in detergent compositions may be employed such as soil-suspending agents, soil-releasing agents, optical brighteners, abrasives, bactericides, tarnish inhibitors, coloring agents, and/or encapsulated or nonencapsulated perfumes.

Especially suitable encapsulating materials are water soluble capsules which consist of a matrix of polysaccharide and polyhydroxy compounds such as described in GB 1,464,616.

Other suitable water soluble encapsulating materials comprise dextrins derived from ungelatinized starch acid esters of substituted dicarboxylic acids such as described in U.S. Pat. No. 3,455,838. These acid-ester dextrins are, preferably, prepared from such starches as waxy maize, waxy sorghum, sago, tapioca and potato. Suitable examples of said encapsulation materials include N-Lok manufactured by National Starch. The N-Lok encapsulating material consists of a modified maize starch and glucose. The starch is modified by adding monofunctional substituted groups such as octenyl succinic acid anhydride.

Antiredeposition and soil suspension agents suitable herein include cellulose derivatives such as methylcellulose, carboxymethylcellulose and hydroxyethylcellulose, and homo- or co-polymeric polycarboxylic acids or their salts. Polymers of this type include the polyacrylates and maleic anhydrideacrylic acid copolymers previously mentioned as builders, as well as copolymers of maleic anhydride with ethylene, methylvinyl ether or methacrylic acid, the maleic anhydride constituting at least 20 mole percent of the copolymer. These materials are normally used at levels of from 0.5% to 10% by weight, more preferably form 0.75% to 8%, most preferably from 1% to 6% by weight of the composition.

Preferred optical brighteners are anionic in character, examples of which are disodium 4,4'-bis-(2-diethanolamino-4-anilino -s- triazin-6-ylamino)stilbene-2:2' disulphonate, disodium 4, - 4'-bis-(2-morpholino-4-anilino-s-triazin-6-ylaminostilbene-2:2'- disulphonate, disodium 4,4'- bis-(2,4-dianilino-s-triazin-6-ylamino)stilbene-2:2'- disulphonate, monosodium 4',4"- bis-(2,4-dianilino-s-tri-azin-6 ylamino) stilbene-2-sulphonate, disodium 4,4'-bis-(2-anilino-4-(N-methyl-N-2-hydroxyethylamino)-s-triazin-6-ylamino) stilbene-2,2'-disulphonate, di-sodium 4,4'-bis-(4-phenyl-2, 1,3-triazol-2-yl)-stilbene-2,2'disulphonate, di-so-dium 4,4'bis(2-anilino-4-(1-methyl-2-hydroxyethylamino)-s-triazin-6-ylami-no)stilbene-2,2'disulphonate, sodium 2(stilbyl-4"-(naphtho-1',2':4,5)-1,2,3, - triazole-2"-sulphonate and 4,4'-bis(2-sulphostyryl)biphenyl.

Other useful polymeric materials are the polyethylene glycols, particularly those of molecular weight 1000–10000, more particularly 2000 to 8000 and most preferably about 4000. These are used at levels of from 0.20% to 5% more preferably from 0.25% to 2.5% by weight. These polymers and the previously mentioned homo- or co-polymeric polycarboxylate salts are valuable for improving whiteness maintenance, fabric ash deposition, and cleaning performance on clay, proteinaceous and oxidizable soils in the presence of transition metal impurities.

Soil release agents useful in compositions of the present invention are conventionally copolymers or terpolymers of terephthalic acid with ethylene glycol and/or propylene glycol units in various arrangements. Examples of such polymers are disclosed in U.S. Pat. Nos. 4,116,885 and 4,711,730 and EP 0 272 033. A particular preferred polymer in accordance with EP 0 272 033 has the formula:

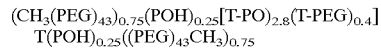
$$T(POH)_{0.25}((PEG)_{43}CH_3)_{0.75}$$

where PEG is —(OC$_2$H$_4$)O—, PO is (OC$_3$H$_6$O) and T is (pOOC6H$_4$CO).

Also very useful are modified polyesters as random copolymers of dimethyl terephthalate, dimethyl sulfoisophthalate, ethylene glycol and 1,2-propanediol, the end groups consisting primarily of sulphobenzoate and secondarily of mono esters of ethylene glycol and/or 1,2-propanediol. The target is to obtain a polymer capped at both end by sulphobenzoate groups, "primarily", in the present context most of said copolymers herein will be endcapped by sulphobenzoate groups. However, some copolymers will be less than fully capped, and therefore their end groups may consist of monoester of ethylene glycol and/or 1,2-propanediol, thereof consist "secondarily" of such species.

The selected polyester s herein contain about 46% by weight of dimethyl terephthalic acid, about 16% by weight of 1,2-propanediol, about 10% by weight ethylene glycol, about 13% by weight of dimethyl sulfobenzoic acid and about 15% by weight of sulfoisophthalic acid, and have a molecular weight of about 3.000. The polyesters and their method of preparation are described in detail in EP 311 342.

Softening agents: Fabric softening agents can also be incorporated into laundry detergent compositions in accordance with the present invention. These agents may be inorganic or organic in type. Inorganic softening agents are exemplified by the smectite clays disclosed in GB-A-1 400898 and in U.S. Pat. No. 5,019,292. Organic fabric softening agents include the water insoluble tertiary amines as disclosed in GB-A1 514 276 and EP 0 011 340 and their combination with mono C$_{12}$–C$_{14}$ quaternary ammonium salts are disclosed in EP-B-0 026 528 and di-long-chain amides as disclosed in EP 0 242 919. Other useful organic ingredients of fabric softening systems include high molecular weight polyethylene oxide materials as disclosed in EP 0 299 575 and 0 313 146.

Levels of smectite clay are normally in the range from 5% to 15%, more preferably from 8% to 12% by weight, with the material being added as a dry mixed component to the remainder of the formulation. Organic fabric softening agents such as the water-insoluble tertiary amines or dilong chain amide materials are incorporated at levels of from 0.5% to 5% by weight, normally from 1% to 3% by weight whilst the high molecular weight polyethylene oxide materials and the water soluble cationic materials are added at levels of from 0.1% to 2%, normally from 0.15% to 1.5% by weight. These materials are normally added to the spray dried portion of the composition, although in some instances it may be more convenient to add them as a dry mixed particulate, or spray them as molten liquid on to other solid components of the composition.

Polymeric dye-transfer inhibiting agents: The detergent compositions according to the present invention may also comprise from 0.001% to 10%, preferably from 0.01% to 2%, more preferably form 0.05% to 1% by weight of polymeric dye-transfer inhibiting agents. Said polymeric dye-transfer inhibiting agents are normally incorporated into detergent compositions in order to inhibit the transfer of dyes from colored fabrics onto fabrics washed therewith. These polymers have the ability of complexing or adsorbing the fugitive dyes washed out of dyed fabrics before the dyes have the opportunity to become attached to other articles in the wash.

Especially suitable polymeric dye-transfer inhibiting agents are polyamine N-oxide polymers, copolymers of N-vinylpyrrolidone and N-vinylimidazole, polyvinylpyrrolidone polymers, polyvinyloxazolidones and polyvinylimidazoles or mixtures thereof.

Addition of such polymers also enhances the performance of the enzymes according the invention.

The detergent composition according to the invention can be in liquid, paste, gels, bars or granular forms. Non-dusting granulates may be produced, e.g., as disclosed in U.S. Pat. No. 4,106,991 and 4,661,452 (both to Novo Industri A/S) and may optionally be coated by methods known in the art. Examples of waxy coating materials are polyethylene oxide) products (polyethyleneglycol, PEG) with mean molecular weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591.

Granular compositions according to the present invention can also be in "compact form", i.e. they may have a relatively higher density than conventional granular detergents, i.e. form 550 to 950 g/l; in such case, the granular detergent compositions according to the present invention will contain a lower amount of "Inorganic filler salt", compared to conventional granular detergents; typical filler salts are alkaline earth metal salts of sulphates and chlorides, typically sodium sulphate; "Compact" detergent typically comprise not more than 10% filler salt. The liquid compositions according to the present invention can also be in "concentrated form", in such case, the liquid detergent compositions according to the present invention will contain a lower amount of water, compared to conventional liquid detergents. Typically, the water content of the concentrated liquid detergent is less than 30%, more preferably less than 20%, most preferably less than 10% by weight of the detergent compositions.

The compositions of the invention may for example, be formulated as hand and machine laundry detergent compositions including laundry additive compositions and compositions suitable for use in the pretreatment of stained fabrics, rinse added fabric softener compositions, and compositions for use in general household hard surface cleaning operations and dishwashing operations.

The following examples are meant to exemplify compositions for the present invention, but are not necessarily meant to limit or otherwise define the scope of the invention.

In the detergent compositions, the abbreviated component identifications have the following meanings:

LAS: Sodium linear $C_{12}$ alkyl benzene sulphonate

TAS: Sodium tallow alkyl sulphate

XYAS: Sodium $C_{1X}$–$C_{1Y}$ alkyl sulfate

SS: Secondary soap surfactant of formula 2-butyl octanoic acid

25EY: A $C_{12}$–$C_{15}$ predominantly linear primary alcohol condensed with an average of Y moles of ethylene oxide 45EY: A $C_{14}$–$C_{15}$ predominantly linear primary alcohol condensed with an average of Y moles of ethylene oxide XYEZS: $C_{1X}$–$C_{1Y}$ sodium alkyl sulfate condensed with an average of Z moles of ethylene oxide per mole Nonionic: $C_{13}$–$C_{15}$ mixed ethoxylated/propoxylated fatty alcohol with an average degree of ethoxylation of 3.8 and an average degree of propoxylation of 4.5 sold under the tradename Plurafax LF404 by BASF Gmbh CFAA: $C_{12}$–$C_{14}$ alkyl N-methyl glucamide TFAA: $C_{16}$–$C_{18}$ alkyl N-methyl glucamide Silicate: Amorphous Sodium Silicate ($SiO_2$:$Na_2O$ ratio= 2.0)

NaSKS-6: Crystalline layered silicate of formula $\delta$-$Na_2Si_2O_5$

Carbonate: Anhydrous sodium carbonate

Phosphate: Sodium tripolyphosphate

MA/AA: Copolymer of 1:4 maleic/acrylic acid, average molecular weight about 80,000

Polyacrylate: Polyacrylate homopolymer with an average molecular weight of 8,000 sold under the tradename PA30 by BASF Gmbh Zeolite A: Hydrated Sodium Aluminosilicate of formula $Na_{12}$ $(AlO_2SiO_2)_{12}$. $27H_2O$ having a primary particle size in the range from 1 to 10 micrometers Citrate: Tri-sodium citrate dihydrate Citric: Citric Acid Perborate: Anhydrous sodium perborate monohydrate bleach, empirical formula $NaBO_2 \cdot H_2O_2$ PB4: Anhydrous sodium perborate tetrahydrate Percarbonate: Anhydrous sodium percarbonate bleach of empirical formula $2Na_2CO_3 \cdot 3H_2O_2$ TAED: Tetraacetyl ethylene diamine CMC: Sodium carboxymethyl cellulose DETPMP: Diethylene triamine penta (methylene phosphonic acid), marketed by Monsanto under the Tradename Dequest 2060

PVP: Polyvinylpyrrolidone polymer

EDDS: Ethylenediamine-N, N'-disuccinic acid, [S,S] isomer in the form of the sodium salt Suds Suppressor: 25% paraffin wax Mpt 50° C., 17% hydrophobic silica, 58% paraffin oil Granular Suds suppressor: 12% Silicone/silica, 18% stearyl alcohol, 70% starch in granular form Sulphate: Anhydrous sodium sulphate HMWPEO: High molecular weight polyethylene oxide TAE 25: Tallow alcohol ethoxylate (25)

Detergent Example I

A granular fabric cleaning composition in accordance with the invention may be prepared as follows:

| | |
|---|---|
| Sodium linear C$_{12}$ alkyl benzene sulfonate | 6.5 |
| Sodium sulfate | 15.0 |
| Zeolite A | 26.0 |
| Sodium nitrilotriacetate | 5.0 |
| Enzyme of the invention | 0.1 |
| PVP | 0.5 |
| TAED | 3.0 |
| Boric acid | 4.0 |
| Perborate | 18.0 |
| Phenol sulphonate | 0.1 |
| Minors | Up to 100 |

Detergent Example II

A compact granular fabric cleaning composition (density 800 g/l) in accord with the invention may be prepared as follows:

| | |
|---|---|
| 45AS | 8.0 |
| 25E3S | 2.0 |
| 25E5 | 3.0 |
| 25E3 | 3.0 |
| TFAA | 2.5 |
| Zeolite A | 17.0 |
| NaSKS-6 | 12.0 |
| Citric acid | 3.0 |
| Carbonate | 7.0 |
| MA/AA | 5.0 |
| CMC | 0.4 |
| Enzyme of the invention | 0.1 |
| TAED | 6.0 |
| Percarbonate | 22.0 |
| EDDS | 0.3 |
| Granular suds suppressor | 3.5 |
| water/minors | Up to 100% |

Detergent Example III

Granular fabric cleaning compositions in accordance with the invention which are especially useful in the laundering of coloured fabrics were prepared as follows:

| | | |
|---|---|---|
| LAS | 10.7 | — |
| TAS | 2.4 | — |
| TFAA | — | 4.0 |
| 45AS | 3.1 | 10.0 |
| 45E7 | 4.0 | — |
| 25E3S | — | 3.0 |
| 68E11 | 1.8 | — |
| 25E5 | — | 8.0 |
| Citrate | 15.0 | 7.0 |
| Carbonate | — | 10 |
| Citric acid | 2.5 | 3.0 |
| Zeolite A | 32.1 | 25.0 |
| Na-SKS-6 | — | 9.0 |
| MA/AA | 5.0 | 5.0 |
| DETPMP | 0.2 | 0.8 |
| Enzyme of the invention | 0.10 | 0.05 |
| Silicate | 2.5 | — |
| Sulphate | 5.2 | 3.0 |
| PVP | 0.5 | — |
| Poly (4-vinylpyridine)-N-Oxide/copolymer of vinyl-imidazole and vinyl-pyrrolidone | — | 0.2 |
| Perborate | 1.0 | — |
| Phenol sulfonate | 0.2 | — |
| Water/Minors | Up to 100% | |

Detergent Example IV

Granular fabric cleaning compositions in accordance with the invention which provide "Softening through the wash" capability may be prepared as follows:

| | | |
|---|---|---|
| 45AS | — | 10.0 |
| LAS | 7.6 | — |
| 68AS | 1.3 | — |
| 45E7 | 4.0 | — |
| 25E3 | — | 5.0 |
| Coco-alkyl-dimethyl hydroxy-ethyl ammonium chloride | 1.4 | 1.0 |
| Citrate | 5.0 | 3.0 |
| Na-SKS-6 | — | 11.0 |
| Zeolite A | 15.0 | 15.0 |
| MA/AA | 4.0 | 4.0 |
| DETPMP | 0.4 | 0.4 |
| Perborate | 15.0 | — |
| Percarbonate | — | 15.0 |
| TAED | 5.0 | 5.0 |
| Smectite clay | 10.0 | 10.0 |
| HMWPEO | — | 0.1 |
| Enzyme of the invention | 0.10 | 0.05 |
| Silicate | 3.0 | 5.0 |
| Carbonate | 10.0 | 10.0 |
| Granular suds suppressor | 1.0 | 4.0 |
| CMC | 0.2 | 0.1 |
| Water/Minors | Up to 100% | |

Detergent Example V

Heavy duty liquid fabric cleaning compositions in accordance with the invention may be prepared as follows:

| | I | II |
|---|---|---|
| LAS acid form | — | 25.0 |
| Citric acid | 5.0 | 2.0 |
| 25AS acid form | 8.0 | — |
| 25AE2S acid form | 3.0 | — |
| 25AE7 | 8.0 | — |
| CFAA | 5 | — |
| DETPMP | 1.0 | 1.0 |
| Fatty acid | 8 | — |
| Oleic acid | — | 1.0 |
| Ethanol | 4.0 | 6.0 |
| Propanediol | 2.0 | 6.0 |
| Enzyme of the invention | 0.10 | 0.05 |
| Coco-alkyl dimethyl hydroxy ethyl ammonium chloride | — | 3.0 |
| Smectite clay | — | 5.0 |
| PVP | 2.0 | — |
| Water/Minors | Up to 100% | |

The invention is described in further detail in the following examples which are not in any way intended to limit the scope of the invention as claimed.

MATERIALS AND METHODS

Deposited organisms:

*Thermoalcalibacter bogoriae* DSM No. 9380 comprises the α-amylase of the invention.

Culturing conditions.

*Thermoalcalibacter bogoriae* was cultivated under anaerobic conditions in the following medium: $(NH_4)_2SO_4$, 1.0; $NH_4Cl$, 0.4; $Na_2S_2O_4$, 0.1; $K_2HPO_4$, 0.5; $MgSO_4$, 0.1; $CaCl_2$, 0.05; NaCl, 10.0; Trypton, 0.25; yeast extract, 0.25; $FeCl_3$, 0.01; Resazurin, 0.001; $NaHCO_3$, 2.2; $Na_2CO_3$, 2.2; Cystein, 0.5, Starch, 5.0, all concentrations in grams per liter. Trace element solution 141, 10 ml/l, vitamine solution 141, 10 ml both solutions prepared as described in the DSM Catalogue of Strains 1993.

Large scale cultivation was done in a 19 liter fermentor (Bioengineering, Wald, Switzerland) under pH regulation at pH 9.0 and 50° C., the culture was stirred at 300 rpm and flushed with $N_2$ at 10 liters/hour. Inocculation of the fermentor was done with one liter of a preculture, grown for 8 hours at 50° C. in a 2 liter flask without shaking.

Purification of amylolytic enzymes.

All purification steps were conducted at room temperature unless otherwise stated. After cultivation in a 19 liter fermentor for 8 hours, the culture broth consisting of 16 liter was centrifuged in a continuous flow centrifuge rotor (Heraeus, Osterode, Germany) at 41C and 12000 rpm until the cells were separated from the culture supernatant. The culture supernatant was subsequently concentrated to give a final volume of 1 liter by cross flow filtration using a 10 kDa filter (Filtron). Further concentration was performed with an Amicon filtration chamber using a 10 kDa filter (Amicon). In order to remove disturbing amounts of $H_2S$ and to change the buffer, the concentrated supernatant was applied to a PD-10 ion exchange column (Pharmacia) and eluated with 100 mM sodium phosphate buffer pH 9.0. The eluate containing amylolytic activity was collected and concentrated 10-fold in an Amicon chamber (10 kDa filter Amicon). Samples of this solution were applied to a Q-Sepharose anion exchange chromatography column (15×2.5 cm) (Pharmacia) preequilibrated with 100 mM sodium phosphate buffer pH 9.0. The column was washed with 90 ml of equilibrating buffer. The enzyme solution was eluated with equlibration buffer containing 1 M NaCl, using a gradient of NaCl from 0 to 300 mM and 300 to 500 mM at a flow rate of 0.2 ml/min. Fractions were collected (2 ml per tube) and their amylolytic activity was determined as described herein. The active fractions were collected, assembled and subsequently 10-fold concentrated in a Amicon chamber. Samples of this prepurified amylase were added to a Superose 75 gel filtration column (Pharmacia) preequilibrated with 50 mM sodium phosphate buffer pH 9.0. The enzyme was eluated with the equilibration buffer at a flow rate of 0.1 ml/min. The fractions were collected (1 ml/tube) and the active fractions were pooled and subsequently concentrated in an Amicon chamber with a 10 kDa membrane.

Electrophoresis and molecular mass determination.

According to Laemmli (Laemmli et al.) sodium dodecyl sulfate polyacrylamide gel electrophoresis (SDS-PAGE) was carried out with 11.5% polyacrylamide gels in a Mini Protean II electrophoresis system (Bio-Rad) at constant current of 24 mA and voltage high. Proteins were silver stained according to Blum et al (Blum et al). In order to determine the molecular weight, a broad range molecular weight protein mixture (Bio-Rad) was used as standard.

Activity staining of amylolytic enzyme activity in SDS-PAGE.

Prior to activity staining, the SDS gel was incubated for 30 min in a 2.5% Triton X-100 solution in order to remove SDS. Amylolytic protein bands were detected by incubating the gel for 10 min at 65° C. in 100 mM sodium phosphate buffer pH 9.0 for amylase, supplemented with 0.5% soluble starch (Merck). Amylase bands were- visualized by staining the gel with a $KJ$-$J_2$ solution (3 g KJ, 2 g $J_2$ per liter aqua dest.), resulting in white activity bands within a brownish background.

Amylolytic assay.

The enzyme assay routinely used was carried out with enzyme solution using the respective prepurified enzyme and substrate solutions at 0.5% soluble starch (Merk, Darmstadt, Germany) or 0.2% amylose or 0.2% amylopectine (each wt/vol) in 100 mM sodium phosphate buffer pH 9.0 to give a final volume of 0.1 ml. Incubation was done for 30 min at 65° C. if not stated 5 otherwise. The amount of reducing sugars was estimated using the Somogyi-Nelson method (Somogyi, M. J. Biol. Chem. (1945) 160:61–68; Nelson, N. J. Biol. Chem. (1944) 153:375–380), enzyme activity was calculated using a standard calibartion curve with 0–1% (wt/vol) maltose One unit (U) of amylolytic activity was defined as the amount of 1 mmol reducing sugars liberated by the enzyme per minute under standard conditions (pH 9.0; 65° C.).

Protein determination.

Protein concentrations were determined by the Lowry 15 method. Microassays were performed and bovine serum albumine was used as standard protein.

Effect of pH and temperature.

To study the influence of pH and temperature on amylase activity, the prepurified enzyme solution was used. 10 ml of the enzyme solution were mixed with 90 ml of a 0.5% (wt/vol) substrate solution (soluble starch; Merck) in 120 mM universal Britton & Robinsson buffer with pH 4.0 to 11.0. The changes in pH due to the mixture of the enzyme solution and substrate solution were measured. After a preincubation for 30 min of this mixture on ice, the enzyme assay was performed at 65° C. for 30 min. The developed reducing sugars were plotted against the respective pH value.

The influence of temperature on amylase activity was studied using the prepurified enzyme. 10 ml enzyme solution were mixed with 90ml of a 0.5% substrate solution (soluble starch; Merck) in 100 mM sodium phosphate buffer at its optimal pH 9.0. Incubation was done for 30 min at temperature between 30° C. and 80° C. To test the temperature stability, enzyme solution in srew-cap Ependorf tubes was incubated at 60° C., 70° C. and 80° C. for up to 21 h and samples were withdrawn at certain time intervals and were used to test for residual amylase activity.

Substrate specificity.

In order to determine the substrate specificity of the a-amylase, the enzyme was incubated with substrate solution (each wt/vol) containing soluble starch (Merck) (0.5%), amylopectin (0.2%), amylose (0.2%), pullulan (0.2%), maltotriose, maltotetraose and maltopentose (each 0.1%). The assay was incubated for 30 min under standard conditions (65° C., pH 8.0). The enzyme activity was determined, in the case of a-amylase, by measuring the amount of reducing sugars.

Analysis of hydrolysis products.

The hydrolysis pattern of amylase action on different substrates were analyzed by high-performance liquid chromatography (HPLC) (Knauer GmbH, Berlin, Germany) with an Aminex-HPX-42 A column (300 by 7.8 mm; Bio-Rad, Hercules, Calif.). One part of the prepurified respective enzyme was incubated together with 9 parts of substrate solution pH 9.0 for amylase, at 65° C. for up to 16 hours.

After incubation the assays were kept frozen at −20° C. until they were analyzed. As substrate solution we utilized soluble starch (0.5%), pullulan (0.5%), amylose (0.2%), amylopectine (0.2%), maltooligosaccharides DP1 to DP5 (DP=degree of polymerization), cyclodextrine mixture (0.1%) and the pure cyclodextrins (a, b, g) each wt/vol in 100 mM sodium phosphate buffer pH 9.0 for amylase.

Chemicals.

Pullulan cyclodextrins and maltooligosaccharides were obtained from Sigma (St. Louis, Mo.). Chemicals for electrophoresis were purchased by Serva (Heidelberg, Germany). Other chemicals were obtained from Merck (Darmstadt, Germany).

EXAMPLE 1

Purification of the amylase.

The specific activity of the amylase in the 70-fold concentrated culture supernatant after cultivation was 0.096 U/mg. Due to the production of $H_2S$ during fermentation, as previously described, a purification using a PD-10 ion exchange column was neccessary in order to remove $H_2S$, sulfides and other activity desturbing agents. After this treatement, the amount of detectable activity was raised to 0.48 U/mg. This effect was regardless to the used method for detection of reducing sugars (data not shown). The concentrated culture supernatant revealed three activity bands in an SDS-PAGE electrophoresis gel (FIG. 1, lane 2) by activity staining. The lowest activity band with an apparent molecular weight of 57±3 kDa was shown to exhibit α-amylase activity (see below). Samples of the 10-fold concentrated PD-10 eluate were applied to a Q-Sepharose anion exchange chromatography column (Pharmacia, Sweden; 25×200 mm) and the column was run at 1.0 ml/min with the equilibration buffer (100 mM sodium phosphate pH 8.0) using the Bio-Rad Econo System. The a-amylase was eluated by a NaCl-gradient up to 500 mM at 250 mM salt. The fractions containing a-amylase activity were collected and combined. A 10-fold concentrated sample of this amylase containing pool (FIG. 1, lane 3) was applied to a Superdex 75 gel filtration column (Pharmacia, Sweden; 15×300 mm) and eluated with a 100 mM sodium phosphate buffer pH 8.0 at a flow rate of 0.1 ml/min using the Bio-Rad Econo System. The active fractions were collected and the concentrate of these could be shown to be electropheretically homogeneous by silver staining. The purified enzyme had a specific activity of 2.8 U/mg protein. The mobility of the silver stained single protein band coincided with that of the active amylase band determined by activity staining (FIG. 1, lane 4 and 5).

EXAMPLE 2

Characterization of the purified amylase:

Molecular mass determination.

The molecular mass of the amylase, determined by the activity stained as well as the silver stained single band was estimated to be 57±3 kDa. (FIG. 1, lane 4 and 5).

Effect of pH and temperature on enzyme activity.

Figure 2:
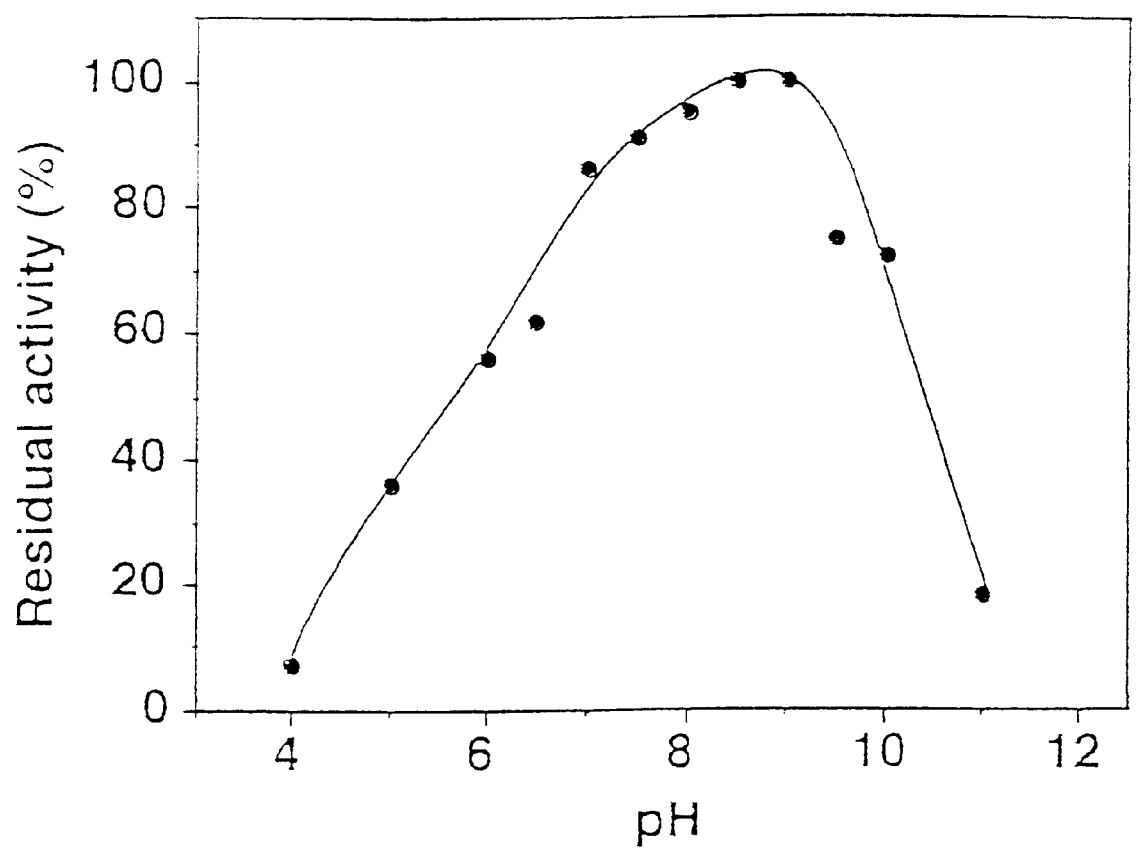
FIG. 2 shows the pH optimum of the prepurified α-amylase from *Thermoalcalibacter bogoriae.* For the determination of the pH optimum universal buffer (Britton & Robinson) pH 4.0–11.0 containing 0.5% (wt/vol) soluble starch was used at 65° C. and 30 minutes incubation time. 100% of residual acitivty correspond to 0.28 U/ml.

The prepurified enzyme exhibited an optimal pH between pH 8.0 and 9.0 with a broad range of activity between pH 5 and 10.5 (FIG. 2). Under the assay conditions (65° C., 60 min) the amylase is stable in between this broad pH range. The optimal pH of the amylase fits with the optimal growth condition of the strain (pH 9.5). After 60 min incubation with 0.5% soluble starch (wt/vol) at the alkaline pH 10.0 the amylase exhibits high stability with only 30% loss of activity (FIG. 2).

Figure 3:
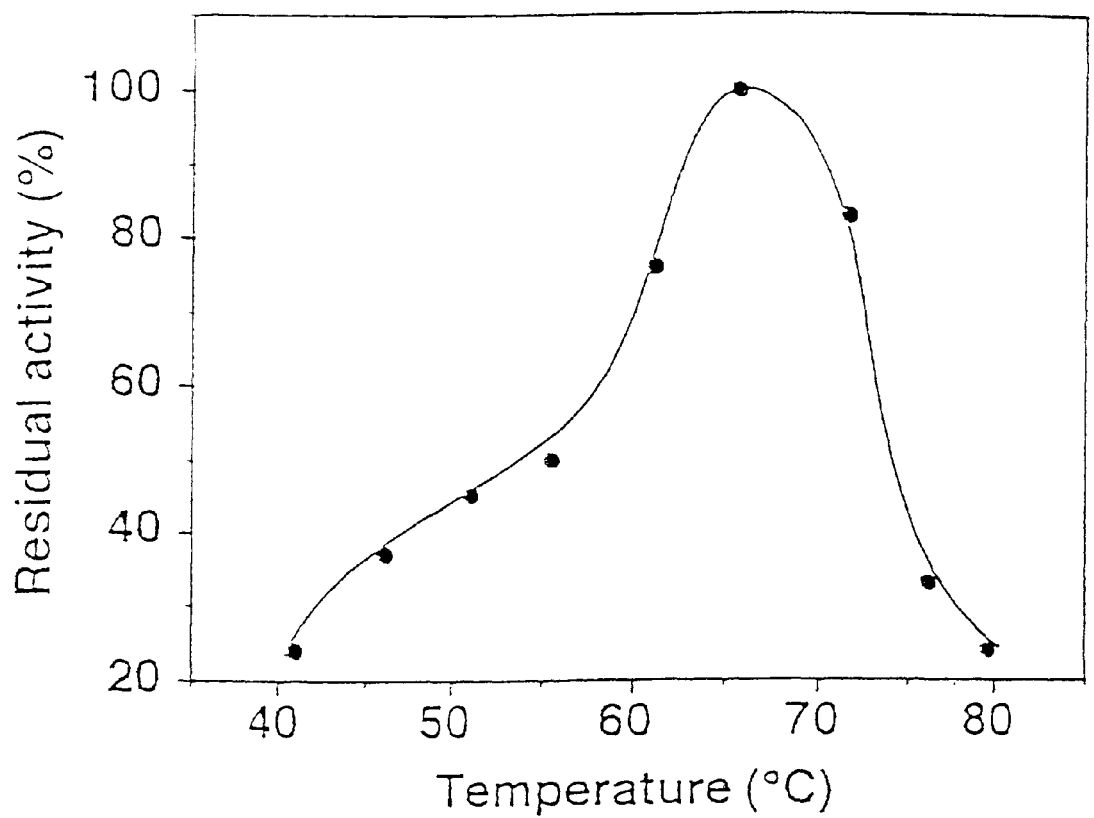
FIG. 3 shows the temperature optimum of α-amylase from *Thermoalcalibacter bogoriae.* Incubation was done for 30 minutes in 100 mM sodium phosphate buffer pH 9.0 containing 0.5% (wt/vol) soluble starch. 100% of residual activity correspond to 0.30 U/ml.

The temperature profile of the prepurified amylase shows distinct optimal temperature for activity at 65° C. (FIG. 3). under the assay conditions, pH 9.0 and 60 min incubation with 0.5% soluble starch, the enzyme exhibits only low activity at temperatures below 45° C. and above 75° C.

Effect of metal ions and chemical reagents.

The amylase activity was measured at pH 8.0 -higher pH would interfere with metal ion solutions- and 65° C. in presence of various metal ions at 1 mM, 2 mM and 5 mM concentration and in presence of some chemical reagents (FIG. 4). Amylase activity was not or only slightly inhibited by the addition of various metal ions such as $Co^{2+}$, $Ca^{2+}$ and EDTA. Moderate inhibition occurred with $Mg^{2+}$, $Mo^{7+}$, $Zn^{2+}$ and $Ni^{2+}$. Strong inhibition was observed by the addition of $Cu^{2+}$, $Fe^{2+}$, $Fe^{3+}$, $V^{4+}$ and $Cr^{6+}$. Although a moderate stimulation of amylase activity could be achieved upon addition of $Mn^{2+}$, the enzyme is active when incubated in 100 mM sodium phosphate buffer only.

The chemical reagents all caused a stimulation on amylase activity at 1 mM concentration (FIG. 4), whereas at 5 mM enzyme activity was totally inhibited upon addition of the protein spreading detergents SDS and DTT. The addition of N-bromosuccinimide caused a 57% inhibition, whereas the serine inhibitor Pefabloc SC did not interfer with amylase activity. A stimulatory effect on amylase activity was still observed with 5 mM Guanidine-HCl.

References

Bender, H.. 1991. Branched saccharides formed by the action of His-modified cyclodextrin glycosyltransferase from *Klebsiella pneumoniae* M 5 al on starch. Carbohydr Res 222:239–244.

Binder, F., O. Huber, and A. Böck. 1986. Cyclodextringlycosyltransferase from *Klebsiella pneumoniae* M5al: cloning, nucleotide sequence, and expression. Gene 47:269–277.

Boyer, E. W., M. B. Ingle, and G. D. Mercer. 1973. *Bacillus alcalophilus* subsp. halodurans subsp. nov.: an alkaline-amylase-producing, alkalophilic organism. Int J Syst Bacteriol 23:238–242.

Canganella, F., C. M. Andrade, and G. Antranikian. 1994. Characterization of amylolytic and pullulytic enzymes from thermophilic archaea and from a new Fervidobacterium species. Appl Microbiol Biotechnol 42:239–245.

Galvin, N. M., C. T. Kelly, and W. M. Fogarty. 1994. Purification and properties of the cyclodextrinase of *Bacillus sphaericus* ATCC 7055. Appl Microbiol Biotechnol 42:46–50.

Grant, W. D., W. E. Mwatha, and B. E. Jones. 1990. Alkaliphiles: ecology, diversity and applications. FEMS Microb Rev 75:255–270.

Grant, W. D., and K. Horikoshi. 1992. Alkaliphiles: ecology and biotechnological applications. In R. A. Herbert and R. J. Sharp (ed.), Molecular biology and biotechnology of extremophiles. Blackie & Son, Glasgow.

Hayashi, T., T. Akiba, and K. Horikoshi. 1988. Production and purification of new maltohexaose-froming amylases from alkalophilic Bacillus sp. H-167. Agric Biol Chem 52:443–448.

Hofmann, B. E., H. Bender, and G. E. Schulze. 1989. Three-dimensional structure of cyclodextrin glycosyltransferase from *Bacillus circulans* at 3.4 Å resolution. J Mol Biol 209: 793–800.

Horikoshi, K.. 1991. General view of alkaliphiles and thermophiles, p. 3–14. In K. Horikoshi and W. D. Grant (ed.), Superbugs: Microorganisms in extreme environments. Springer Verlag, Berlin.

Kambourova, M. S., and E. I. Emanuilova. 1992. Purification and general biochemical properties of thermostable pullulanase from *B. staerothermophilus* G-82. Appl Biochem Biotechnol 33:193–203.

Kanai, H., T. Kobayashi, R. Aono, and T. Kudo. 1995. *Natronococcus amylolyticus* sp. nov., a haloalkaliphilic archaeon. Int J Syst Bacteriol 45:762–766.

Keller, M., F.-J. Braun, R. Dirmeier, D. Hafenbradl, S. Burggraf, R. Rachel, and K.-O. Stetter. 1995. *Thermococcus alcaliphilus* sp. nov., a new hyperthermophilic archaeum growing on polysulfide at alkaline pH. Arch Microbiol 164:390–395.

Kelly, C. T., M. SA. McTigue, E. M. Doyle, and W. M. Fogarty. 1995. The raw starch-degrading alkaline amylase of Bacillus sp. IMD 370. J Ind Microbiol 15:446–448.

Kim, T.-J., B.-C. Kim, and H.-S. Lee. Production of cyclodexttrins using moderately heat-treated cornstarch. Enzyme Microb Technol 17:1057–1061.

Kim, T. U., B. G. Gu, J. Y. Jeong, S. M. Byun, and Y. C. Shin. 25 1995. Purification and characterization of a maltotetraose-froming alkaline α-amylase from an alkalophilic Bacillus strain, GM8901. Appl Environ Microbiol 61:3105–3112.

Koch, R., A. Spreinat, K. Lemke, and G. Antranikian. 1991. Purification and properties of a hyperthermoactive a-amylase from the archaeobacterium *Pyrococcus woesei*. Arch Microbiol 155:572–578.

Lee, J.-E., K.-H. Choi, J.-Y. Choi, Y.-S. Lee, I.-B. Kwon, and J.-H. Yu. 1992. Enzymatic production of a-cyclodextrin with the cyclomaltodextrin gluconotransferase of *Klebsiella oxytoca* 19-1. Enzyme Microb Technol 14:1017–1020.

Leuschner, C., and G. Antranikian. 1995. Heat-stable enzymes from extremely thermophilic and hyperthermophilic microorganisms. World J Microb Biotechnol 11:95–114.

Li, Y., L. Mandelco, and J. Wiegel. 1993. Isolation and characterization of a moderately thermophilic anaerobic alkaliphile, *Clostridium paradoxum* sp. nov.. Int J Syst Bacteriol 43:450–460.

Li, Y., M. Engle, N. Weiss, L. Mandelco, and J. Wiegel. 1994. *Clostridium thermoalcaliphilum* sp. nov., an anaerobic and thermotolerant facultative alkaliphile. Int J Syst Bacteriol 44:111–118.

Lin, J.-M., T. Nakagama, H. Okazawa, X.-Z. Wu, and T. Hobo. 1996. Separation and determination of some stereoisomers by capillary gel electrophoresis with cyclodextrin incorporated in polyacrylamide gel. Fresenius J Anal Chem 354:451–454.

Luong, J. H. T., R. S. Brown, K. B. Male, M. V. Cattaneo, and S. Zhao. 1995. Enzyme reactions in the presence of cyclodextrins: biosensors and enzyme assays. Tibtech 13:457–463.

McTigue, M. A., C. T. Kelly, E. M. Doyle, and W. M. Fogarty. 1995. The alkaline amylase of the alkalophilic Bacillus sp. IMD 370. Enzyme Microb Technol 17:570–573.

Nakamura, N., N. Sashihara, H. Nagayama, and K. Horikoshi. 1989. Characterization of pullulanase and a-amylase activities of a Thermus sp. AMD33. Starch 41:112–117.

Nogrady, N. I. P6csi and A. Szentirmai. 1995. Cyclodextrin glycosyltransferase may be the only starch-degrading enzyme in *Bacillus macerans*. Biotechnol Appl. Biochem 21:233–243.

Norman, B. E. and S. T. Jorgensen. 1992. Thermoanaerobacter sp. CGTase: its properties and application. Denpun Kagaku 39:101–108.

Pedersen, S., B. F. Jensen, L. Dijkhuizen, S. T. Jorgensen, B. W. Dijkstra. 1995. A better enzyme for cyclodextrins. Chemtech December 1995.

Pongsawasdi, P., and M. Yagisawa. 1988. Purification and some properties of cyclodextrin glucanotransferase from *Bacillus circulans*. Agric Biol Chem 52:1099–1103.

Rawyler, A, P. A. Siegenthaler. 1996. Cyclodextrins: a new tool for the controlled lipid depletion of thylakoid membranes. Biochim Biophys Acta 1278:89–97.

Rüdiger, A., P. L. Jorgensen, and G. Antranikian. 1995. Isolation and characterization of a heat-stable pullulanase from the hyperthermophilic archaeon *Pyrococcus woesei* after cloning and expression of its gene in *Escherichia coli*. Appl Environ Microbiol 61:567–575.

Sabioni, J. G. and Y. K. Park. 1992. Production and characterization of cyclodextrin glycosyltransferase from *Bacillus lentus*. Starch 44:225–229.

Saha, B. C. and J. G. Zeikus. 1992. Cyclodextrin degrading enzymes. Starch 44:312–315.

Spreinat, A., and G. Antranikian. 1990. Purification and properties of a thermostable pullulanase from *Clostridium thermosulfurogenes* EMI which hydrolyses both a-1,6 and a-1,4-glycosidic linkages. Appl Microbiol Biotechnol 33:511–518.

Szejtli, J.. 1982. Cyclodextrins in food, cosmetics and toiletries. Starch 34:379–385.

Vetter, D. and W. Thorn. 1992. Chain length specificity of cyclodextrin glycosyltransferase. Starch 44:229–233.

Wind, R. D., W. Liebl, R. M. Buitelaar, D. Penninga, A. Spreinat, L. Dijkhuizen, and H. Bahl. 1995. Cyclodextrin formation by the thermostable α-amylase of *Thermoanaerobacterium thermosufurigenes* EM1 and reclassification of the enzyme as a cyclodextrin glycosyltransferase. Appl Environ Microbiol 61: 1257–1265.

Zhilina, T. N., G. A. Zavarzin, F. Painey, V. V. Kevbrin, N. A. Kostrikina, and A. M. Lysenko. 1996. *Spirochaeta alkalica* sp. nov., *Spirochaeta africana* sp. nov., and *Spirochaeta asistica* sp. nov., alkaliphilic anaerobes from the continental soda lakes in Central Asia and the East African Rift. Int J Syst Bacteriol 46:305–312.

What is claimed is:

1. An isolated α-amylase, wherein said α-amylase:
   1) is obtained from a strain of a Thermoalcalibacter sp.,
   2) has a pH optimum of α-amylase activity in the range from 8.0–9.0,
   3) has at least 65% residual α-amylase activity after 30 min incubation at 65° C., pH 8.0 in a substrate solution containing 0.5% (wt/vol) soluble starch and a $Ca^{2+}$ concentration of 0.5 mM, and
   4) has a temperature optimum of 65±5° C. measured at pH 9.0.

2. The α-amylase according to claim 1, wherein the Thermoalcalibacter sp. is a moderately thermo alkaliphile anaerobe strain.

3. The α-amylase according to claim 2, wherein the strain is *Thermoalcalibacter bogoriae*.

4. The α-amylase according to claim 1, wherein the α-amylase has a molecular mass of 57±3 kDa.

5. A method of producing an α-amylase according to claim 1, the method comprising (i) culturing a strain of Thermoalcalibacter sp under conditions permitting the production of the enzyme, and (ii) recovering the enzyme from the culture.

6. The method according to claim 5, wherein the Thermoalcalibacter sp is a strain of *Thermoalcalibacter bogoriae*.

7. An enzyme composition comprising an α-amylase according to claim 1 and a buffer.

8. The enzyme composition according to claim 7, further comprising an enzyme selected from the group consisting of a protease, a lipase, an additional amylolytic enzyme, an oxidase and a cellulase.

* * * * *